(12) United States Patent
Vinas et al.

(10) Patent No.: US 11,826,547 B2
(45) Date of Patent: Nov. 28, 2023

(54) AUTOMATIC CLOSED-LOOP GLUCOSE CONTROL WITH AN ADAPTIVE MEAL BOLUS CALCULATOR

(71) Applicant: Imperial College Innovations Limited, London (GB)

(72) Inventors: Pau Herrero Vinas, London (GB); Pantelis Georgiou, London (GB); Nick Oliver, London (GB); Christofer Toumazou, London (GB)

(73) Assignee: Imperial College Innovations Limited, London (GB)

( * ) Notice: Subject to any disclaimer, the term of this patent is extended or adjusted under 35 U.S.C. 154(b) by 1247 days.

(21) Appl. No.: 16/329,152

(22) PCT Filed: Jul. 27, 2017

(86) PCT No.: PCT/GB2017/052189
§ 371 (c)(1),
(2) Date: Feb. 27, 2019

(87) PCT Pub. No.: WO2018/042147
PCT Pub. Date: Mar. 8, 2018

(65) Prior Publication Data
US 2019/0192774 A1 Jun. 27, 2019

(30) Foreign Application Priority Data
Aug. 30, 2016 (GB) ...................... 1614676

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ................ A61M 5/1723; A61M 5/142; A61M 2202/07; A61M 2205/50;
(Continued)

(56) References Cited

U.S. PATENT DOCUMENTS 9,919,105 B2 * 3/2018 Yodfat ............... A61B 5/14532
2008/0319381 A1 12/2008 Yodfat et al.
(Continued)

FOREIGN PATENT DOCUMENTS

WO 2009/095908 A2 8/2009
WO 2010/078508 A1 7/2010

OTHER PUBLICATIONS

P. Herrero, P. Pesl, M. Reddy, N. Oliver, P. Georgiou and C. Toumazou, "Advanced Insulin Bolus Advisor Based on Run-To-Run Control and Case-Based Reasoning," in IEEE Journal of Biomedical and Health Informatics, vol. 19, No. 3, pp. 1087-1096, May 2015, doi: 10.1109/JBHI.2014.2331896. (Year: 2015).*
(Continued)

*Primary Examiner* — Etsub D Berhanu
*Assistant Examiner* — Samuel C Kim (57) ABSTRACT

A method of adaptively determining one or more compensation factors in a closed-loop insulin delivery system comprising a continuous glucose level sensor, an insulin pump, and an insulin reservoir, where the system determines an insulin meal bolus taking into account an estimated amount of carbohydrates to be ingested, CHO, a difference between a currently sensed glucose level, G, and a glucose set point, $G_{sp}$, and at least one compensation factor, ICR. The method comprises
for each postprandial time period, t3-t4,
determining a bolus offset value, $B_{extra\_new}$, by,
if the sensed glucose level, G, exceeds a threshold level, Gl, determining a total insulin amount deliv-
(Continued)

ered by the insulin pump over the postprandial time period and setting the bolus offset value, $B_{extra\_new}$, to that total insulin amount, or if the sensed glucose level, G, is less than the threshold level, Gl, determining an offset between the sensed glucose level, G, and the glucose set point, $G_{sp}$, and using that offset to determine the bolus offset value, $B_{extra\_new}$, adapting the compensation factor, ICR, over time using the determined the bolus offset value, $B_{extra\_new}$, in order to minimize the bolus offset value for subsequent postprandial time periods.

6 Claims, 2 Drawing Sheets

(51) Int. Cl.
*A61B 5/00* (2006.01)
*G16H 20/17* (2018.01)
*A61M 5/142* (2006.01)
*G16H 50/20* (2018.01)

(52) U.S. Cl.
CPC ............ *A61M 5/142* (2013.01); *G16H 20/17* (2018.01); *A61M 2202/07* (2013.01); *A61M 2205/50* (2013.01); *A61M 2230/201* (2013.01); *A61M 2230/63* (2013.01); *G16H 50/20* (2018.01)

(58) Field of Classification Search
CPC ........ A61M 2230/201; A61M 2230/63; A61B 5/14532; A61B 5/4839; G16H 20/17; G16H 50/20; G16H 40/63
See application file for complete search history.

(56) References Cited

U.S. PATENT DOCUMENTS

| | | | |
|---|---|---|---|
| 2013/0338630 A1* | 12/2013 | Agrawal | G16H 40/63 604/504 |
| 2014/0066892 A1* | 3/2014 | Keenan | G16H 10/40 604/506 |
| 2014/0081236 A1 | 3/2014 | Wilinska et al. | |
| 2014/0276554 A1* | 9/2014 | Finan | A61M 5/14244 604/504 |
| 2015/0217055 A1* | 8/2015 | Booth | G16H 20/17 604/504 |
| 2016/0030670 A1* | 2/2016 | Fischl | A61M 5/1723 604/504 |
| 2016/0117481 A1* | 4/2016 | Booth | A61B 5/14503 604/502 |

OTHER PUBLICATIONS

Pau Herrero et al., "Enhancing automatic closed-loop glucose control in type 1 diabetes with an adaptive meal bolus calculator—in silico evaluation under intra-day variability", *Computer Methods and Programs in Biomedicine*, vol. 146, Jun. 1, 2017, pp. 125-131.
Pau Herrero et al., "Method for automatic adjustment of an insulin bolus calculator: In silico robustness evaluation under intra-day variability", *Computer Methods and Programs in Biomedicine*, vol. 119, No. 1, Feb. 16, 2015, pp. 1-8.
PCT International Search Report and the Written Opinion dated Dec. 15, 2017, issued in related International Application No. PCT/GB2017/052189 (22 pages).
Combined Search and Examination Report dated Feb. 14, 2017, issued in British Application No. GB1614676.3 (6 pages).
International Preliminary Report on Patentability for Application No. PCT/GB2017/052189 dated Mar. 14, 2019, 15 pages.

* cited by examiner

AUTOMATIC CLOSED-LOOP GLUCOSE CONTROL WITH AN ADAPTIVE MEAL BOLUS CALCULATOR

CROSS REFERENCE TO RELATED APPLICATIONS

This application is a national stage application under 35 U.S.C. § 371 of PCT Application No. PCT/GB2017/052189, filed Jul. 27, 2017, which claims priority of benefit to British Patent Application No. 1614676.3, filed on Aug. 30, 2016. The entire contents of the above-identified applications are incorporated herein by reference.

BACKGROUND

Current prototypes of closed-loop systems for glucose control in type 1 diabetes mellitus (T1DM), also referred to as artificial pancreas systems, require a pre-meal insulin bolus to compensate for delays in subcutaneous insulin absorption in order to avoid initial post-prandial hyperglycemia. Computing such a meal bolus is a challenging task due to the high intra-subject variability of insulin requirements. Most closed-loop systems compute this pre-meal insulin dose by a standard bolus calculation, as is commonly found in insulin pumps. However, the performance of these calculators is limited due to a lack of adaptiveness in front of dynamic changes in insulin requirements. Despite some initial attempts to include adaptation within these calculators, challenges remain.

SUMMARY

We present here a new technique to automatically adapt the meal-priming bolus within an artificial pancreas (AP). The technique consists of using a novel adaptive bolus calculator (ABC) based on Case-Based Reasoning and Run-To-Run control, within an AP controller. Communication between the ABC and the AP systems was required to achieve the desired performance. For testing purposes, the clinically validated Imperial College AP controller was employed.

The proposed ABC-enhanced AP controller (ABC-AP) was evaluated against the same AP system without bolus adaptation. The UVa-Padova T1DM v3.2 system (T1DMS) was used to carry out a three-month in silico study on 11 adult and 11 adolescent virtual subjects taking into account inter- and intra-subject variability of insulin requirements and uncertainty on carbohydrate intake.

Overall, the ABC-enhanced AP controller (ABC-AP) improves glycemic control when compared to its non-adaptive counterpart (AP). In particular, the following statistically significant improvements were found. Adults: mean glucose 142.2±9.4 vs. 131.8±4.2 mg/dl; percentage time in target [70, 180] mg/dl, 82.0±7.0 vs. 89.5±4.2; percentage time above target 17.7±7.0 vs. 10.2±4.1. Adolescents: mean glucose 158.2±21.4 vs. 140.5±13.0 mg/dl; percentage time in target, 65.9±12.9 vs. 77.5±12.2; percentage time above target, 31.7±13.1 vs. 19.8±10.2. Note that no increase in percentage time in hypoglycemia was observed.

Using an adaptive meal bolus calculator within a closed-loop control system has the potential to improve glycemic control in type 1 diabetes when compared to its non-adaptive counterpart.

Aspects of the invention are set out in the appended claims.

DETAILED DESCRIPTION

Type 1 diabetes mellitus (T1DM) is an autoimmune condition characterized by elevated blood glucose levels due to the lack of endogenous insulin production. People with T1DM require exogenous insulin delivery to regulate glucose. Current therapies for T1DM management include the administration of multiple daily injections or continuous insulin infusion with pumps. However, such therapies are still suboptimal and require constant adjustment by the person with T1DM and/or by carers. A closed-loop control system consisting of a continuous glucose sensor, an insulin pump and an algorithm that computes the required insulin dose at any instant [Trevitt 2015], has the potential to improve glucose control in people with T1DM.

Recent studies evaluating a closed-loop system for automatic glucose control in type 1 diabetes mellitus (T1DM), also referred to as artificial pancreas, have demonstrated safety and efficacy during in-clinic and ambulatory trials [Thabit 2015].

Figure 1:
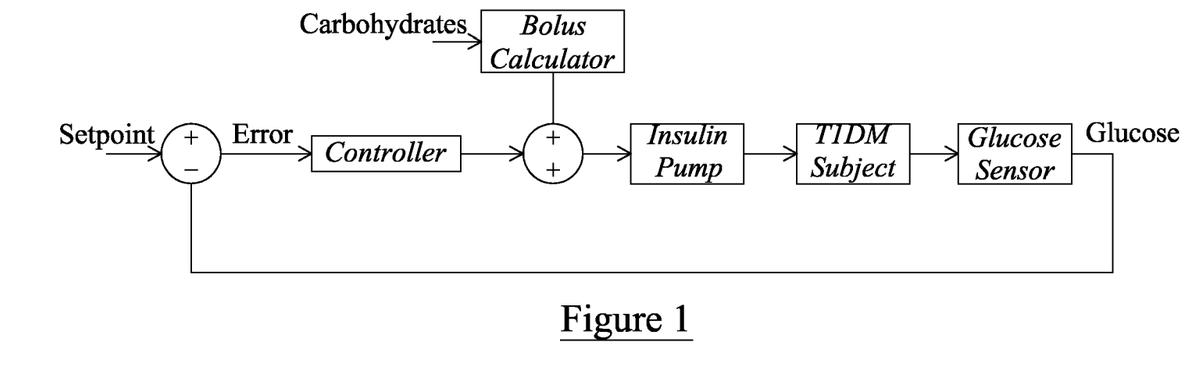
FIG. 1 illustrates schematically a closed loop controller incorporating a meal bolus calculator.

Ideally, a completely automated closed-loop control system would not require any user intervention, for example to announce meals, and would react in real-time to changes in blood glucose. However, delays in subcutaneous insulin absorption have led many investigators to include the use of a pre-meal insulin bolus within the artificial pancreas [Doyle 2014]. FIG. 1 is a block diagram of a closed-loop system for glucose control incorporating a meal bolus calculator. The calculation of such pre-meal insulin bolus is usually done by means of a simple bolus calculator [Schmidt 2014], found in most insulin pumps. However, accurately computing a meal bolus remains a challenging task due to the high variability of insulin requirements in T1DM [Visentin 2015] and the uncertainty in carbohydrate estimations [Brazeau 2013].

The utilisation of an adaptive meal-priming bolus within an artificial pancreas has previously been proposed by El-Khatib et. al [El-Khatib 2015], and shows some encouraging clinical results relative to an entirely reactive system with no meal-priming boluses. Such adaptive meal-priming insulin bolus consists of automatically adjusting the size of breakfast, lunch, and dinner doses by administering 75% of the average prandial insulin provided for previous meals at that time of day. However, this method has the limitation that assumes that carbohydrate intakes are fairly similar every day, which is not always the case. It also does not take into consideration other factors such as exercise, alcohol, stress, weather, hormones, and variation in macronutrient composition.

Here we present a novel technique to automatically adjust the meal-priming bolus within an artificial pancreas that overcomes these limitations, by allowing the system to consider an estimation of the carbohydrate intake and other parameters affecting glucose outcomes. The proposed technique is based on an existing adaptive bolus calculator, referred to as Advanced Bolus Calculator for Diabetes (ABC4D) [Herrero 2015a, Herrero 2015b, Pesl 2016, Reddy 2016], which has been modified to fulfill the requirements of a closed-loop system for blood glucose control.

For evaluation purposes, a novel version of the clinically validated Imperial College Bio-inspired AP controller [Herrero 2012, Reddy 2014, Reddy 2015] (see Appendix A below) and the UVa-Padova T1DM v3.2 system (T1DMS) simulation platform [Kovatchev 2009] were employed.

Insulin Bolus Calculator

A standard insulin bolus calculator [Schmidt 2014] is defined by the equation $$B = \frac{CHO}{ICR} + \frac{(G - G_{sp})}{ISF} - IOB, \quad (1)$$

where B (U) is the total calculated bolus, CHO (g) is the estimated amount of ingested carbohydrates, ICR (g/U) is the insulin-to-carbohydrate-ratio, G (mg/dl) is the measured glucose at meal time, $G_{sp}$ (mg/dl) is the glucose set-point, ISF (mg/dl/U) is the insulin sensitivity factor, and IOB (U) is the insulin-on-board, which represents an estimation of the remaining active insulin in the body [Schmidt 2014].

The parameters of a bolus calculator (ICR, ISF) can be manually adjusted based on the time of the day (i.e. breakfast, lunch, dinner), exercise, or variation in hormonal cycles. However, these adjustments are often crude approximations and are rarely revised by the users (subject with T1DM or carer) on a regular basis.

In order to provide the required adaptability within a bolus calculator to be able to cope with the significant intra-subject variability in T1DM management, a Case-Based Reasoning approach [Aamodt 1994] was proposed by Herrero and colleagues [Herrero 2015a].

An Adaptive Insulin Bolus Calculator

The proposed adaptive meal bolus calculator for closed-loop control is based on an existing technique referred to as Advanced Bolus Calculator for Diabetes Management (ABC4D) [Herrero 2015a, Herrero 2015b]. ABC4D has previously been validated in silico [Herrero 2015a, Herrero 2015b] and tested in clinical trials [Pesl 2016, Reddy 2016].

ABC4D enhances currently existing bolus calculators by means of a combination of Case-Based Reasoning [Aamodt 1994] and Run-To-Run Control [Wang 2009]. Periodic use of continuous glucose monitoring (CGM) data is required in order to perform a retrospective optimization of the bolus calculator parameters as described in [Herrero 2015b].

Case-Based Reasoning

Case-Based Reasoning (CBR) is an artificial intelligence problem solving framework that solves a newly encountered problem (i.e. meal insulin dosing), based on the information obtained from previously solved problems (cases). CBR is usually described in four steps: Retrieve the most similar cases from a case-base (e.g. late dinner preceded by moderate exercise); Reuse solutions of retrieved cases (e.g. bolus calculator parameters ICR and ISF); Revise the outcome of the applied solution (e.g. post-prandial glucose excursion); and Retain the new solution (e.g. adapted ICR and ISF parameters) if considered useful for solving future problems [Aamodt 1994].

In ABC4D, cases are stored in a case-base representing meal scenarios with significantly different insulin requirements (e.g. breakfast after exercise vs. dinner after watching a movie) and therefore, requiring a different insulin dosing.

It is important to note that, unlike the traditional CBR approach where the solution of the cases in the case-base is static, in ABC4D such a solution (i.e. ICR and ISF) is adapted if considered to be sub-optimal. This strategy partially solves the so-called problem of cold-start in CBR [Quijano-Sánchez 2012] by allowing the case-base to be initialized with known case solutions (e.g. ICR and ISF used by the subject) and let the system converge towards an optimal solution while adding new cases to the case-base if considered different enough. In order to perform the adaptation of sub-optimal solutions for each case within the case-base, the Run-to-Run algorithm proposed in [Herrero 2015b] is employed.

Run-To-Run Algorithm

Run-To-Run (R2R) is a control methodology designed to exploit repetitiveness in the process that is being controlled [Wang 2009]. Its purpose is to enhance performance, using a mechanism of trial and error. The simplest formulation of R2R may be, $$u_{k+1} = u_k + K \cdot \text{error}, \quad (2)$$

where u is the control action, K is a tuning gain and error is the tracking error defined as the difference between a measurement from the process and a set-point.

The R2R algorithm used in ABC4D is based on the hypothesis that the meal insulin bolus can be adjusted based on the residual between the minimal post-prandial glucose concentration ($G_{min}$), obtained with a continuous glucose monitor, and a predefined glucose set-point ($G_{sp}$) over a predefined time window [t1, t2]. Therefore, the adjusted bolus is calculated as $$B_{k+1} = B_k + K \cdot (G_{min} - G_{sp}), \quad (3)$$

where $B_{extra} = K \cdot (G_{min} - G_{sp})$ is the extra insulin that needs to be added (or subtracted) to the original bolus ($B_k$) in order to bring blood glucose levels back to the set-point ($G_{sp}$), and K is defined as K~1/ISF.

In order to provide robustness to the metric against the inherent variability and uncertainty of the system (e.g. sensor noise and carbohydrate estimation), a glucose range [$G_l$, $G_h$] is defined where no adaptation is done if $G_{min}$ falls within this range. For the same reason, the second term of equation Equation (1) (i.e. correction bolus) is considered to be zero if G falls within the glucose range [$G_l$, $G_h$].

The ABC4D R2R algorithm is based on a second hypothesis that sustains that insulin-to-carbohydrate-ratio (ICR) and insulin sensitivity factor (ISF) are correlated [Walsh 2011] by the expression $$ISF = \frac{1960 ICR}{2.6W}, \quad (4)$$

where W is the weight of the subject (lbs). Thus, from Equation (1), the ICR parameter can be updated according to the equation $$ICR_{k+1} = \frac{CHO + \frac{G - G_{sp}}{(1960/2.6W)}}{(B_k + B_{extra}) + IOB}. \quad (5)$$

However, Equation (5) is not fully suited to be used within the context of a closed-loop (CL) system for blood glucose control. Note that the CL controller can compensate for the lack of meal-priming bolus and bring glucose levels within the target range [$G_l$, $G_h$] over the time window [t1, t2], but the post-prandial glucose peak can still be significantly sub-optimal. Nonetheless, assuming that the CL controller is correctly tuned, the ABC4D R2R metric is still valid when $G_{min}$ falls below the target range. If $G_{min}$ falls within or above the target range, a new metric for adjusting ICR is required.

The new proposed metric is based on the hypothesis that, assuming that the CL controller is appropriately tuned, the insulin delivered by the CL controller during the postprandial period over the basal insulin, is insulin that should have been delivered by the meal-priming bolus. Thus, the bolus calculator parameters can be updated based on this additional insulin.

Let the insulin delivered by the CL controller over the basal insulin during the postprandial period [t2, t3] be defined as $$B_{extra\_new} = \begin{cases} \min\left(\sum_{t3}^{t4} D(t), k*B\right), & \text{if } G > Gl; \\ K \cdot (Gmin - Gsp), & \text{if } G < Gl, \end{cases} \quad (6)$$

where $D(t)$ are the individual insulin doses delivered by the CL controller and k a tunable gain to saturate $B_{extra}$ to a maximum dose of k*B. Then, the updated ICR ($ICR_{k+1}$), and consequently $ISF_{k+1}$, can be easily obtained by replacing $B_{extra}$ by $B_{extra\_new}$ in Equation (5). Note that, since the objective is to bring glucose levels within the target range $[G_l, G_h]$, only the insulin delivered over $G>G_h$ is considered in Equation (6). Also, the time intervals for calculating $B_{extra\_new}$ can be different depending if $G>Gh$ or $G<Gl$.

Finally, to further improve the robustness of the proposed metric, the new ICR is obtained by computing the average of two consecutive ICR adaptations and the current value. Therefore, actual adaptations are only carried out every two adaptations for the same meal case.

For this study, the following values were considered for the evaluation of the proposed R2R algorithm: $G_l=80$ mg/dl; $G_h=120$ mg/dl; $G_{sp}=100$ mg/dl; $t_1=2$ h; $t_2=5$ h, $t_3=2$ h; $t_4=4$ h, k=0.2. The rational for choosing such time windows was the fact that it usually takes about 2 hours to be able to say that a meal bolus is not enough to cover a meal due to the slow insulin pharmacokinetics (i.e. insulin-on-board), and that a postprandial glucose excursion for a standard mixed meal lasts around 4 to 5 hours.

Finally, in order to integrate the presented adaptive meal bolus calculator (ABC) within a closed-loop (CL) controller two additional considerations need to be taken into account. First, since both the CL controller and the ABC include mechanisms to prevent insulin overdosing (i.e. insulin-on-board and insulin feedback), the insulin-on-board (IOB) from Equation (1) and Equation (5) were omitted. Second, since the CL controller is supposed to correct hyperglycemia during fasting condition, the correction bolus term from Equation (1) (i.e. second term) was omitted when $G>G_l$.

The reader is referred to Appendix A for details about the Imperial College Artificial Pancreas controller employed in this study.

In Silico Evaluation Under Intra-Day Variability

The latest version of the UVa-Padova T1DM simulator (v3.2) (Kovatchev 2009) was used to evaluate the proposed adaptive bolus calculator for closed-loop controllers. 11 adult subjects and 11 adolescent subjects were used for this purpose. The chosen basal insulin infusion rate for the virtual subjects was the one provided by the default insulin therapy of the simulator. The selected CGM and insulin pump models to perform the simulations were the Dexcom G4 and Deltec Cozmo. A three-month scenario was selected in order to leave enough time to the meal bolus adaptation mechanism to converge.

Intra-day variability was introduced to the simulator by modifying some of the parameters of the model described in [Dalla Man 2007]. In particular, meal variability was emulated by introducing meal-size variability (CV=10%), meal-time variability (STD=20) and uncertainty in the carbohydrate estimation (uniform distribution between −30% and +20%) [Brazeau 2013]. Meal absorption rate ($k_{abs}$) and carbohydrate bioavailability (f) were considered to be ±30% and ±10% respectively. The 11 meals corresponding to each cohort were randomly assigned at each meal intake. Intra-subject variability in insulin absorption model parameter ($k_d$, $k_{a1}$, $k_{a2}$) was assumed ±30% [Haidar 2013]. Insulin sensitivity parameters ($V_{mx}$, $K_{p3}$) were assumed to vary along the day following the sinusoidal pattern $$p(t) = p_0 + 0.3 \cdot p_0 \sin\left(2\frac{\pi}{24 \cdot 60}\right)t + 2\pi \cdot RND, \quad (7)$$

where $p(t)$ is the corresponding time varying parameter (i.e. $V_{mx}$ or $k_{p3}$); p0 is the default parameter value in the simulator; and RND is a randomly uniformly generated number between 0 and 1.

The selected daily pattern of carbohydrate doses was 7 am (60 g), 12 pm (100 g) and 6 pm (80 g).

Note that despite all the variability introduced in the simulator, only three different cases were required within the CBR algorithm (i.e. breakfast, lunch and dinner).

In order to test the benefits of the proposed technique, the Imperial College Artificial Pancreas (AP) controller with the adaptive meal bolus calculator (ABC-AP) was evaluated against the same controller without meal bolus adaptation (AP).

The following standard glycemic control metrics were selected for comparison purposes: mean blood glucose (BG); percentage time in target range [70, 180] mg/dl (% inT); percentage time below target (%<T); percentage time above target (%>T); risk index (RI); low blood glycemic index (LBGI); high blood glycemic index (HBGI); and daily average of insulin delivered in units of insulin (TDI).

Results

Figure 2:
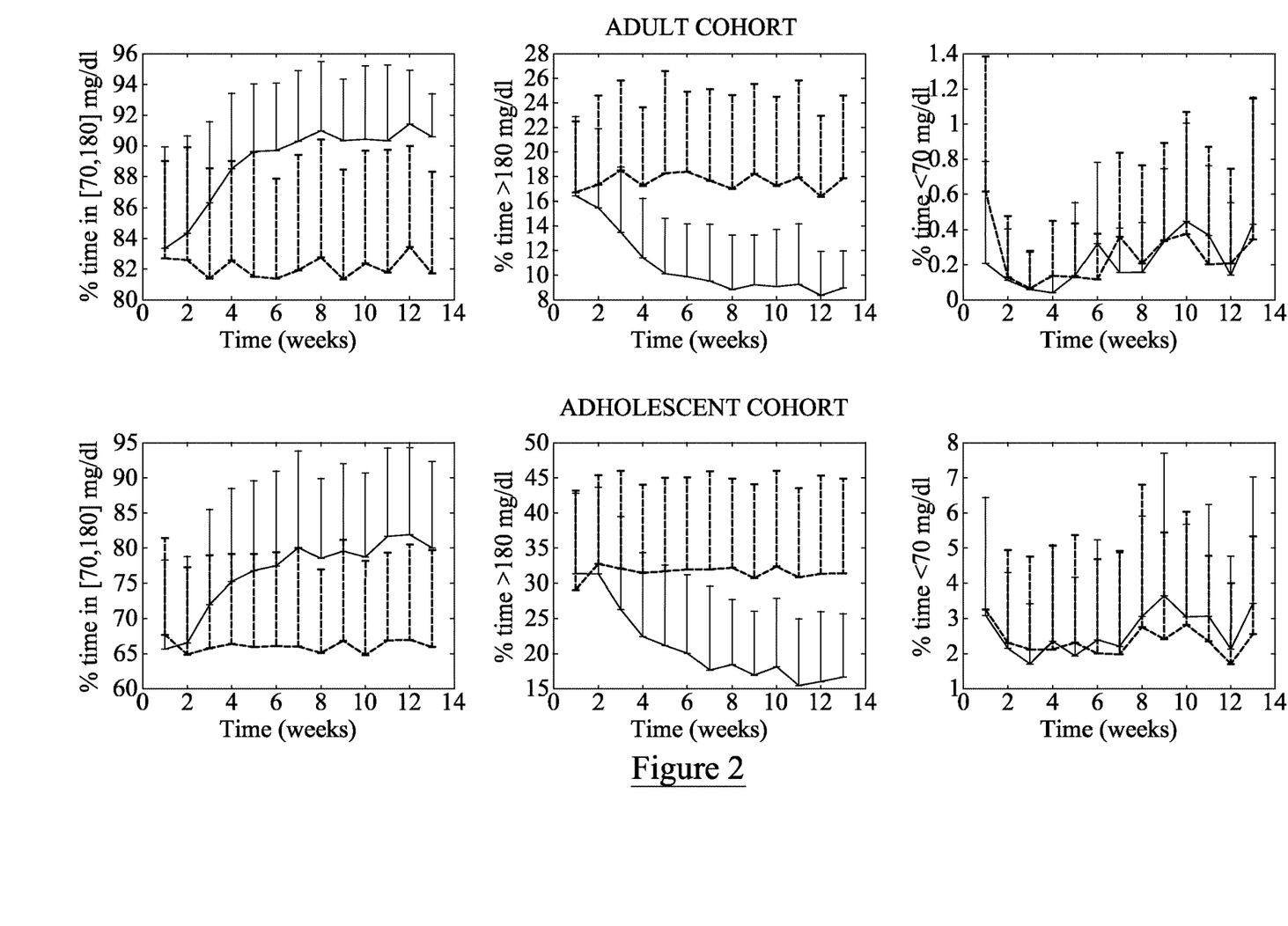
FIG. 2 shows prior art and adaptive meal bolus calculations for adult and adolescent cohorts.

Table 1 and Table 2 show the results corresponding to the 11 adults and 11 adolescents for each one of the evaluated control strategies (AP vs. ABC-AP). FIG. 2 shows a comparison between AP and ABC-AP of the weekly evolution of three of the evaluated glycemic metrics (% inT, %<T and %>T) for the two studied cohorts.

TABLE 1

| | Glycemic results corresponding to the 11 adult subjects. | | | | | | | |
|---|---|---|---|---|---|---|---|---|
| | BG | % inT | % < T | % > T | RI | LBGI | HBGI | TDI |
| AP | 142.2 ± 9.4 | 82.0 ± 7.0 | 0.21 ± 0.36 | 17.7 ± 7.0 | 3.7 ± 1.3 | 0.14 ± 0.12 | 3.6 ± 1.3 | 45.8 ± 10.1 |
| ABC-AP | 131.8 ± 4.2 | 89.5 ± 4.2 | 0.21 ± 0.18 | 10.2 ± 4.1 | 2.4 ± 0.69 | 0.19 ± 0.06 | 2.2 ± 0.6 | 48.5 ± 10.4 |
| p | <0.001 | <0.001 | 0.99 | <0.001 | <0.005 | 0.12 | <0.005 | 0.002 |

TABLE 2

Glycemic results corresponding to the 11 adolescent subjects.

|        | BG           | % inT        | % < T       | % > T        | RI          | LBGI         | HBGI        | TDI         |
|--------|--------------|--------------|-------------|--------------|-------------|--------------|-------------|-------------|
| AP     | 158.2 ± 21.4 | 65.9 ± 12.9  | 2.2 ± 2.7   | 31.7 ± 13.1  | 7.8 ± 3.9   | 0.73 ± 0.82  | 7.0 ± 3.9   | 35.0 ± 8.8  |
| ABC-AP | 140.5 ± 13.0 | 77.5 ± 12.2  | 2.5 ± 2.4   | 19.8 ± 10.2  | 5.2 ± 3.1   | 0.94 ± 0.84  | 4.2 ± 2.4   | 38.3 ± 10.2 |
| p      | <0.001       | <0.001       | 0.6446      | <0.001       | <0.001      | 0.4          | <0.001      | <0.001      |

FIG. 2 shows the weekly evolution of the glycemic metrics % inT, %<T and %>T for the adult cohort (above) and the adolescent cohort (below) corresponding the AP controller without meal bolus adaptation (dashed red line) and the AP controller with meal bolus adaptation (ABC-AP) method (solid blue line). Error bars represent the standard deviation.

Integrating an adaptive meal bolus calculator within the Imperial College Artificial Pancreas controller (ABC-AP) significantly improves all the evaluated glycemic outcomes in a virtual T1D population (11 adults+11 adolescents) when compared against the Imperial College AP without bolus adaptation over a three-month scenario with intra-day variability. It is important to note that the proposed adaptive meal bolus calculator is independent of the closed-loop controller employed and could be used within other artificial pancreas systems.

It is also worth noting that the significant reduction in hyperglycemia was achieved without any increase in hypoglycemia—indeed in both the adult and adolescent there was a non-significant reduction in time spent below target.

Despite the significant intra-subject variability and uncertainty in carbohydrate intake estimation, the closed-loop controller was able to cope avoid remarkably well with hypoglycemia. Therefore, the inclusion of the adaptive meal bolus calculator did not introduce any improvement regarding time spent in hypoglycemia.

Although statistically significant, the increase in total daily insulin delivered was not dramatically relevant (i.e. 3 U per day on average). This is an indicator that for this study, the most important factor for improving glycemic control is the way insulin was delivered and not the total amount.

When analyzing the weekly evolution of the evaluated glycemic metrics, it was observed that glycemic metrics take about 8 weeks to converge without significant oscillations towards a steady state value and remain fairly stable along the simulation. This convergence rate could be increased by using a less conservative strategy when saturating/filtering the insulin-to-carbohydrate ratio adaptation.

In a real-life scenario, the convergence rate might take longer due to the consideration of more cases representing other scenarios such as exercise, alcohol consumption, hormone cycles or stress.

Thanks to the additional intra-day variability introduced in the simulator, it was possible to evaluate the robustness of the proposed technique under conditions which might be not too far from a real-life scenario. Clinical trials to evaluate such a technique are currently in preparation.

Appendix A—The Imperial College Artificial Pancreas Controller

The Imperial College Artificial Pancreas (ICAP) controller has been previously in silico and clinically validated [Herrero 2012, Reddy 2014, Reddy 2015]. The original ICAP controller has as core component a mathematical model of the beta-cell physiology [Pedersen 2010]. In addition, it incorporates an insulin feedback term [Steil 2004] to avoid insulin stacking by compensating for delays associated with subcutaneous insulin delivery. It also includes a low-glucose suspend (LGS) to minimize hypoglycemia.

In this work, an updated version of ICAP is introduced, where the original pancreatic insulin secretion model [Pedersen 2010] is replaced by a most recent model [Riz 2014]. The motivation for changing such model was its better performance in simulation studies as well as the reduced complexity of the new model which significantly speeds up the computations.

The updated version of the ICAP controller is described by the equation $$u(t)=SR(t)+SR_b-K_y I_p(t), \qquad (8)$$

where SR is the pancreatic insulin secretion (SR) above basal secretion, $SR_b$ is the basal insulin secretion, and $K_y I_p$ is the insulin feedback term, which is proportional ($K_y$) to the plasma insulin estimation $I_p$.

As described in [Riz 2014], the pancreatic insulin secretion (SR) above basal secretion ($SR_b$) is assumed proportional (m) to the amount X of readily releasable insulin in the beta-cells $$SR(t)=m\,X(t). \qquad (9)$$

The change in the insulin amount in the ready releasable pool (RRP) X results from the balance between the insulin secretion rate, the provision Y of insulin refilling the readily releasable pool, and recruitment of readily releasable insulin $X_D$ $$\frac{dX(t)}{dt} = -mX(t) + Y(t) + X_D(t), \qquad X(0)=0, \qquad (10)$$

where $X_D$ is responsible for the first phase of secretion and is assumed to be proportional to the rate of increase of glucose via the constant parameter $K_D$ and expressed as $$X_D(t) = \begin{cases} K_D \dfrac{dG(t)}{dt}, & \text{if } \dfrac{dG(t)}{dt} > 0; \\ 0, & \text{otherwise} \end{cases} \qquad (11)$$

Remark: In the ICAP controller, the conditional statement in Equation (11) regarding the sign of the glucose derivative was eliminated. The rationale behind this modification is that delays in insulin absorption and glucose sensing due to the subcutaneous route make reducing insulin delivery when glucose is dropping desirable in order to minimize hypoglycemia.

The provision Y generates the slower second phase and is controlled by glucose according to the equation $$\frac{dY(t)}{dt} = -\alpha[Y(t) - \beta(G(t) - G_b)], \qquad Y(0)=0, \qquad (12)$$

where $G_b$ represents the basal value of glucose, and α and β are parameters.

Parameter β is employed as a personalised tunable gain proportional to the subject's insulin sensitivity factor (ISF) used to overcome inter-subject variability. In particular, the following correlation was employed for this study, β=0.0225/ISF, where IFS is expressed in mg/dl per U.

Figure 3:
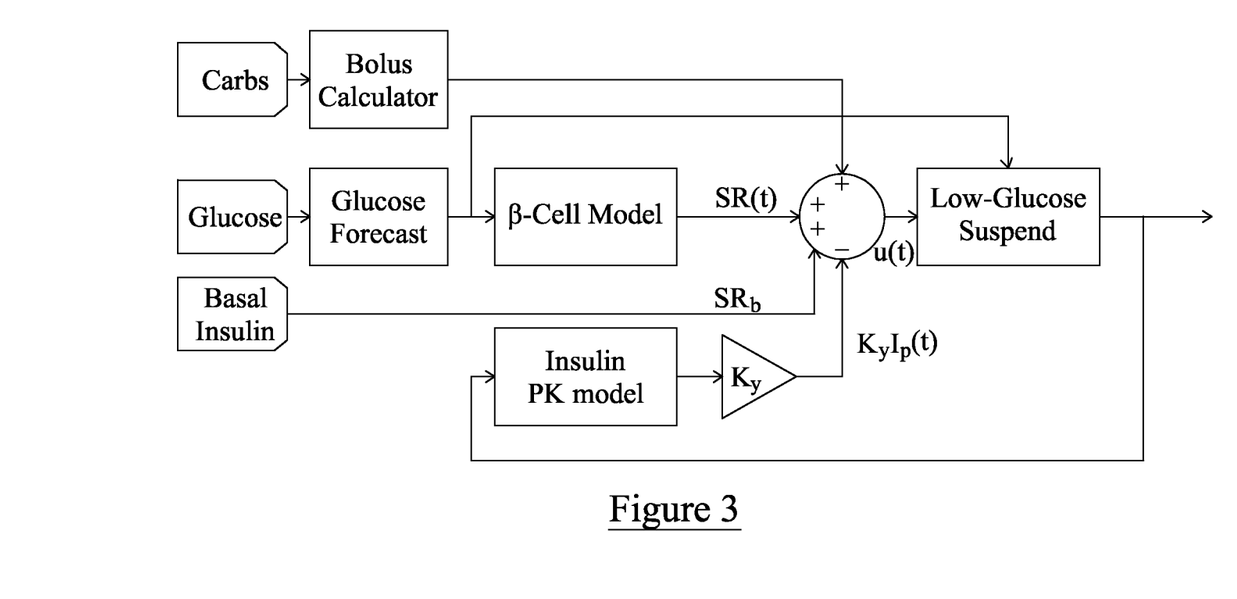
FIG. 3 illustrates schematically an alternative closed loop controller incorporating a meal bolus calculator.

Referring to FIG. 3, the block "β-Cell Model" solves equation (12) over time to obtain Y(t) and then solves equation (10) over time to obtain X(t).

As discussed above, $I_p(t)$ is the plasma insulin estimation after a subcutaneous insulin injection which can be calculated as proposed by Hovorka et al [Hovorka 2004].

$$\frac{dS_1(t)}{dt} = w(t) - \frac{S_1(t)}{t_{max_I}} \quad (13)$$

$$\frac{dS_2(t)}{dt} = \frac{S_1(t)}{t_{max_I}} - \frac{S_2(t)}{t_{max_I}} \quad (14)$$

$$\frac{dI_p(t)}{dt} = \frac{S_2(t)}{V_I t_{max_I}} - k_e I_p(t) \quad (15)$$

where $k_e$ is the first-order decay rate for insulin in plasma, w(t) is the subcutaneous insulin infusion rate, $V_1$ is the distribution volume of plasma insulin, $t_{maxI}$ is the time to maximum insulin absorption, and $S_1(t)$ and $S_2(t)$ are a two-compartment chain representing absorption of subcutaneously administered short-acting (e.g., lispro) insulin.

Referring to the block "Insulin PK model", this solves equation (15) over time to obtain $I_p(t)$.

For simulation purposes, the model was discretized using Euler method with an integration step of one minute. To attenuate the delays associated with subcutaneous glucose sensing [Facchinetti 2014], glucose measurements are forecasted 20 minute ahead using a linear regression of the last 6 glucose values (i.e. the preceding 30 minutes). The basal insulin term ($SR_b$) is set to the subject's basal insulin infusion profile. To tackle the perturbation introduced by the meals, a meal announcement strategy is used consisting of giving an insulin bolus calculated using a standard bolus calculator [Schmidt 2014] immediately before the ingestion of the meal.

To minimise hypoglycaemia, a low-glucose suspend (LGS) algorithm is incorporated on top of the controller. This LGS algorithm reduces the insulin delivery proposed by the controller to 50% if the forecasted glucose value falls below a predefined threshold (TH1) and suspends the insulin delivery if it falls below a second lower predefined threshold (TH1). To prevent rebound hyperglycaemia, the insulin suspension is limited to 90 minutes, after which time the insulin delivery is resumed to 50% for 30 minutes and after this period total suspension is activated again if the hypoglycaemic condition is satisfied. It is important to remark that the LGS algorithm does not affect the meal bolus insulin. FIG. 2 shows a schematic diagram of the ICAP controller.

FIG. 3 is a block diagram of the ICAP controller, where inputs are the amount of ingested carbohydrates, the glucose concentration from a continuous glucose sensor, and the basal insulin rate for a given subject, and the output in the insulin dose to be delivered by the insulin pump.

Table 3 shows the values for the controller parameters employed for the simulation performed in this study. Such parameters where selected based on in silico tests. mean The mean population presented in [Hovorka 2004] were considered for the employed insulin absorption pharmacokinetic (PK) model to estimate plasma insulin concentration ($I_p$).

TABLE 3

Values for the parameters employed for the simulation performed in this study

| Parameter | Value |
| --- | --- |
| m | 0.5 |
| α | m |
| β (U per mg/dl) | 0.0225/ISF |
| $K_D$ (min) | β · 45 |
| $G_b$ (mg/dl) | 117 |
| $K_y$ | 50 |
| TH1 (mg/dl) | 81 |
| TH2 (mg/dl) | 99 |

REFERENCES

[Thabit 2015] Thabit H et al. Home Use of an Artificial Beta Cell in Type 1 Diabetes. N Engl J Med 2015; 373:2129-2140

[Trevitt 2015] Trevitt S, Simpson S, Wood A. Artificial Pancreas Device Systems for the Closed-Loop Control of Type 1 Diabetes: What Systems Are in Development? J Diabetes Sci Technol. 2015. [Epub ahead of print]

[Doyle 2014] Francis J. Doyle, III, Lauren M. Huyett, Joon Bok Lee, Howard C. Zisser and Eyal Dassau. Closed-Loop Artificial Pancreas Systems: Engineering the Algorithms. Diabetes Care. 2014 May; 37(5): 1191-1197.

[Schmidt 2014] Signe Schmidt, Kirsten Nørgaard, Bolus Calculators, J Diabetes Sci Technol September 2014 vol. 8 no. 5 1035-1041.

[Dalla Man 2014] Visentin R, Dalla Man C, Kudva Y C, Basu A, Cobelli C. Circadian variability of insulin sensitivity: physiological input for in silico artificial pancreas. Diabetes Technol Ther. 2015 January; 17(1):1-7.

[Mehta 2009] Sanjeev N. Mehta, Nicolle Quinn, Lisa K. Volkening, and Lori M. B. Laffel. Impact of Carbohydrate Counting on Glycemic Control in Children With Type 1 Diabetes Diabetes Care. 2009 June; 32(6): 1014-1016.

[El-Khatib 2014] El-Khatib F H, Russell S J, Magyar K L, Sinha M, McKeon K, Nathan D M, Damiano E R. Autonomous and continuous adaptation of a bihormonal bionic pancreas in adults and adolescents with type 1 diabetes. J Clin Endocrinol Metab. 2014 May; 99(5): 1701-11.

[Herrero 2015a] Herrero P, Pesl P, Reddy M, Oliver N, Georgiou P, Toumazou C. Advanced insulin bolus advisor based on run-to-run control and case-based reasoning. IEEE J Biomed Health Inform. 2015; 19(3):1087-1096.

[Herrero 2015b] Herrero P, Pesl P, Bondia J, et al. Method for automatic adjustment of an insulin bolus calculator: in silico robustness evaluation under intra-day variability. Comput Methods Programs Biomed. 2015; 119(1):1-8.

[Pesl 2016] Pesl P, Herrero P, Reddy M, et al. An advanced bolus calculator for type 1 diabetes: system architecture and usability results. IEEE J Biomed Health Inform. 2016; 20(1):11-17.

[Pesl 2016] Pesl P, Herrero P, Reddy M, Oliver N, Johnston D G, Toumazou C, Georgiou P. Case-Based Reasoning for Insulin Bolus Advice: Evaluation of Case Parameters in a Six-Week Pilot Study. J Diabetes Sci Technol. 2016 [Epub ahead of print]

[Reddy 2016] M. Reddy et al. Clinical safety and feasibility of the Advanced Bolus Calculator for Type 1 Diabetes (ABC4D): a 6-week non-randomised pilot study. Diabetes Technology and Therapeutics. 2016 [Epub ahead of print].

[Herrero 2012] Herrero P, Georgiou P, Oliver N, Johnston D, Toumazou C. A bio-inspired glucose controller based on pancreatic β-cell physiology. J Diabetes Sci Technol. 2012. 6:606-615.

[Reddy 2014] Reddy M, Herrero R, El Sharkawy M, et al. Feasibility study of a Bio-inspired Artificial Pancreas in adults with type 1 diabetes. Diabetes Technol Ther. 2014; 16:10-17.

[Reddy 2015] Reddy M, Herrero P, Sharkawy M E, Pesl P, Jugnee N, Pavitt D, Godsland I F, Alberti G, Toumazou C, Johnston D G, Georgiou P, Oliver N S. Metabolic Control With the Bio-inspired Artificial Pancreas in Adults With Type 1 Diabetes: A 24-Hour Randomized Controlled Crossover Study. J Diabetes Sci Technol. 2015 Nov. 17; 10(2):405-13.

[Wang 2009] Youqing Wang, Furong Gaoc, Francis J. Doyle III. Survey on iterative learning control, repetitive control, and run-to-run control. Journal of Process Control. 2009. 19(10):1589-1600.

[Aamodt 1994] A. Aamodt and E. Plaza, Case-based reasoning: Foundational issues, methodological variations, and system approaches, AI Commun. 1994. 7:39-59.

[Walsh 2011] J. Walsh, R. Roberts, T. Bailey, Guidelines for optimal bolus calculator settings in adults, J. Diabetes Sci. Technol. 5 (1) (2011) 129-135.

[Kovatchev 2009] B. P. Kovatchev, M. Breton, C. Dalla-Man, C. Cobelli, In silico preclinical trials: a proof of concept in closed-loop control of Type 1 diabetes, J. Diabetes Sci. Technol. 3 (1) (2009) 44-55.

[Pedersen 2010] Pedersen M G, Toffolo G M, Cobelli C. Cellular modeling: insight into minimal models of insulin secretion. Am J Physiol Endocrinol Metab. 2010; 298: 597-601.

[Steil 2004] Steil G M, Panteleon A E, Rebrin K. Closed-loop insulin delivery—the path to physiological glucose control. Adv Drug Deliv Rev. 2004; 56(2)125-44

[Hovorka 2004] Hovorka R, Canonico V, Chassin L J, Haueter U, Massi-Benedetti M, Orsini Federici M, Pieber T R, Schaller H C, Schaupp L, Vering T, Wilinska M E. Nonlinear model predictive control of glucose concentration in subjects with type 1 diabetes. Physiol Mea. 2004; 25(4):905-20.

[Facchinetti 2004] Andrea Facchinetti, Simone Del Favero, Giovanni Sparacino, Jessica R. Castle, W. Kenneth Ward, and Claudio Cobelli. Modeling the Glucose Sensor Error EEE Transactions On Biomedical Engineering, Vol. 61, No. 3, March 2014

[Riz 2014] Riz M, Pedersen M G, Toffolo G M, Haschke G, Schneider H C, Klabunde T, Margerie D, Cobelli C. Minimal modeling of insulin secretion in the perfused rat pancreas: a drug effect case study. Am J Physiol Endocrinol Metab. 2014 March; 306(6):E627-34. 2014.

[Brazeau 2013] A. S. Brazeau, H. Mircescu, K. Desjardins, C. Leroux, I. Strychar, J. M. Ekoé, R. Rabasa-Lhoret, Carbohydrate counting accuracy and blood glucose variability in adults with Type 1 diabetes, Diabetes Res. Clin. Pract. 99 (1) (2013) 19-23.

[Quijano-Sánchez 2012] Lara Quijano-Sánchez, Derek Bridge, Belén Díaz-Agudo, Juan A. Recio-Garcia. A. Case-Based Solution to the Cold-Start Problem in Group Recommenders. Case-Based Reasoning Research and Development. Volume 7466 of the series Lecture Notes in Computer Science pp 342-356. 2012

[Dalla-Man 2007] C. Dalla-Man, R. A. Rizza, C. Cobelli, Meal simulation model of the glucose-insulin system, IEEE Trans. Biomed. Eng. 54 (10) (2007) 1740-1749.

[Haidar 2013] A. Haidar, D. Elleri, K. Kumareswaran, L. Leelarathna, J. M. Allen, K. Caldwell, H. R. Murphy, M. E. Wilinska, C. L. Acerini, M. L. Evans, et al., Pharmacokinetics of insulin as part in pump-treated subjects with Type 1 diabetes: reproducibility and effect of age, weight, and duration of diabetes, Diabetes Care. 36 (10) (2013) e173-e174.

The invention claimed is:

1. A method of controlling a closed-loop insulin delivery system comprising a continuous glucose level sensor, an insulin pump, and an insulin reservoir, where the system determines an insulin meal bolus taking into account an estimated amount of carbohydrates to be ingested, CHO, a difference between a currently sensed glucose level, G, and a glucose set point, $G_{sp}$, and a compensation factor, ICR, the method comprising:

for each postprandial time period,
  determining a bolus offset value, $B_{extra\_new}$, by,
    if the sensed glucose level, G, exceeds a floor threshold level, Gl, of a target range, determining a smaller value between (1) a total insulin amount delivered by the insulin pump over the postprandial time period and (2) a maximum dose of insulin, and setting the bolus offset value, $B_{extra\_new}$, to the determined smaller value, or
    if the sensed glucose level, G, is less than the floor threshold level, Gl, determining an offset between the sensed glucose level, G, and the glucose set point, $G_{sp}$, and setting the bolus offset value, $B_{extra\_new}$, based on the offset,
adapting the compensation factor, ICR, over time using the determined bolus offset value, $B_{extra\_new}$, in order to minimize the bolus offset value for subsequent postprandial time periods; and
in response to an input indicating a need for the insulin meal bolus, determining the insulin meal bolus using the adapted compensation factor, and controlling the insulin pump to deliver the determined insulin meal bolus.

2. The method according to claim 1, where the system determines the insulin meal bolus, denoted as B, according to the equation:

$$B = \frac{CHO}{ICR} + \frac{(G - G_{sp})}{ISF}$$

where ISF (mg/dl/U) is an insulin sensitivity factor, and wherein the second term of the equation is omitted if G is greater than the floor threshold level Gl.

3. The method according to claim 2, where the insulin sensitivity factor, ISF, is determined according to the equation:

$$ISF = \frac{K1 \, ICR}{K2W}$$

where K1 and K2 are predefined constants and W is the weight of a subject.

4. The method according to claim 3, wherein the step of adapting the compensation factor, ICR, over time comprises, for a given postprandial time period, determining an updated compensation factor, $ICR_{k+1}$, according to the equation:

$$ICR_{k+1} = \frac{CHO + \frac{G - G_{sp}}{(K1/K2W)}}{(B_k + B_{extra\_new*})}$$

where $B_k$ is a previously delivered bolus, and $B_{extra\_new*}$ is equal to $B_{extra\_new}$ determined for the given postprandial time period following delivery of the bolus $B_k$, or an average of $B_{extra\_new}$ values obtained over a plurality of postprandial time periods following delivery of the bolus $B_k$.

5. The method according to claim 1, further comprising defining a set of insulin meal bolus cases associated with respective distinct glucose control scenarios including meal types, exercise regimes, time of day, psychological stress, illness, and hormone cycles, and adapting the compensation factor, ICR, separately for each of the insulin meal bolus cases.

6. A controller for use with a closed-loop insulin delivery system comprising a continuous glucose level sensor and an insulin pump having an insulin reservoir, where the system determines an insulin meal bolus taking into account an estimated amount of carbohydrates to be ingested, CHO, a difference between a currently sensed glucose level, G, and a glucose set point, $G_{sp}$, and a compensation factor, ICR, the controller being configured to perform operations including:

computing, for each postprandial time period, a bolus offset value, $B_{extra\_new}$, by, if the sensed glucose level, G, exceeds a floor threshold level, Gl, of a target range, determining a smaller value between (1) a total insulin amount delivered by the insulin pump over the postprandial time period and (2) a maximum dose of insulin, and setting the bolus offset value, $B_{extra\_new}$, to the determined smaller value, or if the sensed glucose level, G, is less than the threshold level, Gl, determining an offset between the sensed glucose level, G, and the glucose set point, $G_{sp}$, and setting the bolus offset value, $B_{extra\_new}$, based on the offset, adapting the compensation factor, ICR, over time using the determined bolus offset value, $B_{extra\_new}$, in order to minimize the bolus offset value for subsequent postprandial time periods; and in response to an input indicating a need for the insulin meal bolus, determining the insulin meal bolus using the adapted compensation factor, and controlling the insulin pump to deliver the determined insulin meal bolus.

* * * * *